United States Patent [19]

Williams et al.

[11] Patent Number: 4,985,385

[45] Date of Patent: Jan. 15, 1991

[54] METHOD OF PREPARING A CATALYST PRECURSOR COMPRISED OF CALCINED NICKEL-ALUMINUM FEITKNECHT COMPOUND/NON-CALCINED ALUMINO-SILICATE CLAY/ALKALINE EARTH AND/OR REAR EARTH METAL COMPOUND

[75] Inventors: Alan Williams, West Midlands; John D. Wilson, Essex; Roger D. Wragg, West Midlands; Stephen D. Jones, Worcester; Costa Komodromos; Timothy J. Reynolds, both of London, all of England

[73] Assignee: British Gas plc, London, England

[21] Appl. No.: 412,298

[22] Filed: Sep. 25, 1989

[30] Foreign Application Priority Data

Sep. 23, 1988 [GB] United Kingdom ............... 8822469

[51] Int. Cl.$^5$ ............................................. B01J 21/16
[52] U.S. Cl. ...................... 502/84; 502/303; 502/320; 502/330; 502/335; 502/341; 502/344
[58] Field of Search ............... 502/84, 330, 335, 341, 502/346, 303, 320, 344

[56] References Cited

U.S. PATENT DOCUMENTS

| | | | |
|---|---|---|---|
| 4,185,967 | 1/1980 | Komodromos et al. | 502/314 |
| 4,216,123 | 8/1980 | Banks et al. | 502/325 |
| 4,217,295 | 8/1980 | Friedrich et al. | 502/84 |
| 4,250,060 | 2/1981 | Banks et al. | 502/330 |
| 4,393,262 | 7/1983 | Kaeding | 585/467 |

FOREIGN PATENT DOCUMENTS

| | | | |
|---|---|---|---|
| 1509557 | 5/1978 | United Kingdom | 502/335 |
| 1573706 | 8/1980 | United Kingdom | 502/335 |
| 2139520A | 11/1984 | United Kingdom | 502/84 |

*Primary Examiner*—Anthony McFarlane
*Attorney, Agent, or Firm*—Larson and Taylor

[57] ABSTRACT

A catalyst precursor is prepared by intimately mixing a nickel-aluminium Feitknecht compound with a non-calcined aluminosilicate clay mineral and at the same time and/or subsequently with at least one additive comprising an alkaline earth and/or rare earth metal compound. The resulting mixture is then calcined to produce the catalyst precursor which can be reduced to the catalyst form. The catalyst may be used, for example, in the methanation of gases and the presence of the additive reduces silicon species loss from the catalyst during use.

31 Claims, No Drawings

METHOD OF PREPARING A CATALYST PRECURSOR COMPRISED OF CALCINED NICKEL-ALUMINUM FEITKNECHT COMPOUND/NON-CALCINED ALUMINO-SILICATE CLAY/ALKALINE EARTH AND/OR RARE EARTH METAL COMPOUND

The present invention relates to catalysts, to catalyst precursor; preparation thereof and to the use of catalysts in gas phase reactions, in particular, in the methanation of gases containing hydrogen and carbon oxides.

The methanation of gases, such as gases obtained from coal gasification processes, may be conducted under conditions which involve high carbon oxide content and the presence of considerable amounts of steam. Such methanation processes are highly exothermic and high temperatures are involved. Catalysts for use in such methanation processes should be capable of retaining both adequate activity and strength.

We have previously found that the mechanical strength of nickel-alumina catalysts for use in such methanation process may be considerably improved by the incorporation of silicates in the form of clays during preparation of the catalysts, for example, as we describe in GB patent specification Nos. 2139520 A and 2166661 A. However, we have found that whilst these catalysts also have good resistance to sintering at high temperatures, there is tendency for steam-volatile silicon species to be leached out of the catalyst. Although the activity of these catalysts may also remain high for long periods, it is possible that a build up of deposits of silica emanating from the steam-volatile silicon species may result and cause problems, such as fouling in pipework downstream of a methanation reactor.

It has now been found that catalyst precursors (i.e. ones in their oxidic or non-reduced form) containing silicates for strengthening the catalyst can be prepared so as to provide a catalyst having a reduced propensity for silicon species loss.

Thus, according to one aspect of the invention, a method of preparing a catalyst precursor comprises intimately mixing a Feitknecht compound (as hereinafter defined) with a non-calcined alumino-silicate clay mineral and, at the same time and/or subsequently but prior to calcination, with at least one stabilising additive for reducing silicon-species loss comprising an alkaline earth and/or rare earth metal compound, and, optionally, an alkali metal compound, and thereafter calcining the resulting mixture to produce a calcined reaction product forming the catalyst precursor.

In this specification the Feitknecht compound has the general formula:

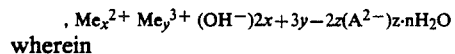

wherein $Me^{2+}$ is substantially completely $Ni^{2+}$,
$Me^{3+}$ is substantially completely $Al^{3+}$ or substantially $Al^{3+}$ and $Cr^{3+}$,
$A^{2-}$ is either a single divalent anion or two monovalent anions.

$x/y$ lies between 1.5/1 and 4/1. The preferred ratio of total divalent metal ion to total trivalent metal ion is 2.8 to 3.2:1, and more preferably 3:1. When $Cr^{3+}$ is present, the preferred atomic ratio of $Cr^{3+}$ to $Al^{3+}$ is up to 1:10.

Also $z/(x+y)$ lies in the range 0.05 to 0.2 and $n/(x+y)$ lies in the range 0.25 to 1.0.

The term "calcined reaction product" is used herein to indicate that there has been sufficient reaction between the components for there to be bonding present between components of the clay mineral and the Feitknecht compound such that discrete particles of Feitknecht compound and clay mineral no longer exist. The term therefore does not necessarily mean that there has been complete reaction between the components.

The Feitknecht compound is formed by co-precipitation comprising the bringing together of a mixed solution of water soluble salts of nickel and aluminium, and optionally chromium, and a precipitant solution. The mixed salt solution may, for example, be a mixed nitrate solution. The precipitant solution may be an alkaline solution such as sodium carbonate, bicarbonate or hydroxide; or potassium carbonate, bicarbonate or hydroxide; or ammonium hydroxide or bicarbonate; or urea.

The intimate mixing of the Feitknecht compound and the clay mineral may be effected by co-precipitating the Feitknecht compound in the presence of the clay mineral. The additive can be mixed in subsequent to the co-precipitation. The clay mineral may be mixed with the precipitant solution, and the resulting precipitant/clay mineral mixture and mixed salt solution brought together. Alternatively, the clay mineral may be mixed with the mixed salt solution, and the resulting mixed salt/clay mineral mixture and precipitant solution brought together. Further alternatively, the mixed salt solution and precipitant solution may be added separately but simultaneously to an aqueous slurry of the clay mineral.

Instead of coprecipitating the Feitknecht compound in the presence of the clay mineral, the Feitknecht compound may be coprecipitated in the absence of the clay mineral and subsequently intermixed or blended with a said additive and the clay mineral. Conveniently, the clay mineral may be in the form of an aqueous slurry, suspension or dispersion, but may be in solid form when brought together with the Feitknecht compound which itself may conveniently be in the form of an aqueous slurry.

Prior to calcining, the said resulting mixture of Feitknecht compound, clay mineral and stabilising additive may be autoclaved in a closed vessel.

The clay mineral may be a naturally occurring one or a synthetic one. It is within the scope of this invention for two or more clay minerals to be present in the resulting mixture to be calcined.

Preferably, the clay mineral is a layer-structured phyllosilicate or pseudo-layer-structured clay mineral. One preferred method of preparation is to co-precipitate the Feitknecht compound in the presence of a layer-structured or pseudo-layer-structured clay mineral. This method is a preferred one because it is believed that the structural similarity between the brucite-like layers of the Feitknecht compounds and phyllosilicate layers of such clays facilitates intimate intermixing by enabling the phyllosilicate layers of the clay mineral to form interlayers with the layers of the Feitknecht compound.

For example, the layer-structured type clay minerals which may be used are the smectites such as bentonite and montmorillonite, and the kaolins or kandites such as kaolinite. Other examples of the layer-structured type minerals are the chlorites or illites. Moreover, the clay mineral may be a mixed layer kind, i.e. comprising two or more different layer-structured type clay minerals inter-layered together.

One example of a pseudo-layer-clay mineral is attapulgite which is made up of chain structures which become associated to form sheets, thus the reason for being referred to herein as a "pseudo-layered-structure". Another example is sepiolite.

The at least one additive compound may be a metal oxide or a water soluble salt of a metal, such as a nitrate, carbonate or hydroxide. For example, the additive compound may be MgO, Mg(OH)$_2$, MgCO$_3$, Mg(NO$_3$)$_2$, CaO, BaO, cerium nitrate, cerium oxide, lanthanum oxide, lanthanum nitrate, yttrium oxide or yttrium nitrate.

The at least one additive compound may be in the form of an aqueous solution, slurry, suspension, dispersion or powdered solid.

In order to incorporate the additive compound into a mixture of the Feitknecht compound and clay mineral, the additive compound may be blended into this mixture either as a solid compound, for example, magnesium oxide or as a solution of a soluble alkali, alkaline earth or rare earth metal compound, such as magnesium nitrate or potassium carbonate which may subsequently be decomposed to a oxide during calcination.

Alternatively, if the Feitknecht compound is formed in the presence of the additive compound the latter should be a solid substantially insoluble compound, such as magnesium oxide, which may be blended into the mixed salt solution, preferably a nitrate solution, or into the precipitant solution, for example, a carbonate, prior to the precipitation of the Feitknecht compound.

The clay mineral itself may in some cases provide the additive compound in a non-simple form, that is as an integral part of the structure of the clay mineral complex. Such clay minerals may be used alone to provide the additive compound or, preferably, one or more separately added additive compounds may be used. For example, the additive compound may be a magnesium oxide species which is present in attapulgite, in which case it is preferable that further separately added magnesium compound is also used.

In a preferred method, the Feitknecht compound and the clay mineral are mixed with an alkaline earth additive and, optionally, with at least one alkali metal additive compound and/or at least one rare earth metal additive compound. For example, in a particularly preferred method, the alkaline earth compound may be a magnesium compound, such as magnesium oxide, whilst the alkali and rare earth metals may be potassium and/or lanthanum.

In order that the catalyst may be further strengthened, the catalyst precursor may be mixed with a cement binder. Preferably, the calcined catalyst precursor is blended with high alumina cement, such as that known by the name of "Secar" and made by the Lafarge Aluminous Cement Company. This cement is particularly suitable since it has a low content of iron, and other components damaging to catalysts. Alternatively, the cement may be blended with the resulting intimate mixture prior to calcination to produce the catalyst precursor mixed with the cement binder.

The clay mineral may be a modified or pre-treated clay mineral of more open structure, for example, an acid-treated or -washed, swelled or expanded; or pillared clay mineral. It is believed that the more open structures of the modified clay minerals facilitate intimate mixing with the Feitknecht compound and thus the reactivity therebetween.

The acid treatment or washing and swelling processes are especially applicable to the layer-structured and pseudo-layer structured clay mineral. For example, Smectite group clays, such as bentonite, may be used in their natural form or in modified form. These "expandible layer clays" may be swelled, when dispersed in alkalis, cation-exchanged or activated by treatment with mineral acids to produce more reactive and versatile forms of these clays.

The clay mineral content of the calcined catalyst precursor may be from 2.5 to 50% and is preferably from 10 to 30% taken on a wt/wt percentage basis of the calcined catalyst precursor, as are all of the figures given in this specification, unless otherwise stated. The clay mineral content figures are determined from measured silicon content of the calcined catalyst precursor and knowledge of the clay mineral used in the preparation of the precursor.

Where the additive is substantially solely an alkaline earth metal or substantially solely a rare earth metal or is a combination of alkaline earth metal and rare earth metal, the additive metal(s) content is preferably from 1 to 27%. Where magnesium is the alkaline earth metal, its content is preferably from 2.0 to 8.0%. Where an alkali additive compound is used with an alkaline earth additive compound, the alkali metal content is preferably not more than about 2.0%.

If the clay mineral is kaolin, then where the sole additive compound is a lanthanum compound the lanthanum content is preferably from 10 to 20%; and where the sole additive compound is a calcium compound the calcium content is preferably from 6 to 15%.

If the clay mineral is kaolin, then where both magnesium and lanthanum additive compounds are used, the combined magnesium and lanthanum content is preferably from 2 to 24%, the magnesium content more preferably being from about 2 to 4%, and the lanthanum content more preferably being from 9 to 20%. If the clay mineral is kaolin, bentonite or montmorillonite, then where both magnesium and potassium additive compounds are used, the magnesium content is preferably from about 2 to 4%, and the potassium content is preferably from 0.5 to 1.0%, or where potassium and sodium additive compounds are used the combined alkali content is preferably up to 1.2%, for example, 0.7% potassium and 0.5% sodium.

Where the catalyst precursor also includes blended in cement, the precursor preferably contains from 5 to 15% clay mineral and from 10 to 40% cement, more preferably from 20 to 35% cement. Where a magnesium compound is used as the additive, the cement containing precursor preferably contains from 2 to 8% magnesium.

The catalyst may be made by reducing the catalyst precursor according to known techniques. For example, the precursor may be contacted with hydrogen gas at a pressure of from atmospheric pressure up to 70 bar and at a temperature of about 500° C.

A passivated catalyst may be prepared by passivating a reduced catalyst in dilute oxygen, or a mild oxidising atmosphere such as a carbon-dioxide containing gas or a mixture of oxygen and nitrogen, or a mixture of air and nitrogen.

The catalyst may be used in a process for the production of methane-containing gases, wherein a mixture of hydrogen and oxides of carbon with or without steam are passed over the catalyst at a temperature of from 250°-750° C.

The catalyst may also be used in a process of steam reforming normally liquid or gaseous hydrocarbons wherein the hydro-carbons and steam are passed at elevated temperature over the catalyst to produce a methane-containing gas.

Moreover, the catalyst may be used in a process for de-enrichment of natural gas, wherein natural gas containing higher hydrocarbons, and steam are passed at elevated temperature over the catalyst to increase the methane content of the gas. The term "higher hydrocarbons" includes ethane, propane and butane.

Furthermore, the catalyst may be used in a process of gasifying methanol and/or ethanol wherein methanol and/or ethanol and steam are passed at elevated temperature over the catalyst to produce a methane-containing gas.

The following examples illustrate in the invention :

Example 1 comparative (catalyst 1) of catalyst containing nickel oxide alumina and Kaolin but no additive to reduce silicon loss. To prepare the catalyst precursor 10kgs of nickel nitrate hexahydrate and 30kg of aluminium nitrate nonahydrate were dissolved in 76 liters of deionised water and heated to 90° C. 2.5kg of Kaolin were added to this solution which was stirred until a uniform suspension was obtained. To this suspension was added over a period of about 1 hour a solution of 25.5 kg anhydrous potassium carbonate in 38 liters of deionised water. The suspension was vigorously stirred throughout and its temperature maintained between 85° and 90° C. When precipitation was complete, the resulting slurry was filtered and the filter cake reslurried with 140 liters of deionised water at 60° to 80° C. The process of reslurrying and filtration was continued until the filtrate contained less than 100 ppm by weight of potassium. A total of three reslurries was required. The final filter cake was dried at 125° C. and calcined in air at 450° C. for 2 hours to give the calcined catalyst precursor. The calcined catalyst precursor was ground to pass a 850 micron sieve, blended with 2 weight % graphite and then pelleted. The composition of the final catalyst precursor is given in Table 1.

Example 2 comparative (catalyst 2) of catalyst containing nickel oxide, alumina and kaolin but no additive to reduce silicon loss. To prepare the catalyst precursor 582g of nickel nitrate hexahydrate and 250g of aluminium nitrate nonahydrate were dissolved in 2 liters of distilled water and heated to 60° C. 420g of anhydrous potassium carbonate was dissolved in a further 1.5 liters of distilled water and to this solution was added 108.2g of a kaolin dispersion (English China Clay RLO 2720, equivalent dry clay content 70g). This solution was heated to 60° C. and the catalyst was precipitated at a constant temperature of 60° C. by slow addition of the carbonates solution to the nitrates solution with stirring. When precipitation was complete, the resulting slurry was filtered and the filter cake reslurried with 2 liters distilled water at 60° C. The process of reslurrying followed by filtration was repeated until the pH of the filtrate dropped below 7. The product was then dried at 125° C. overnight and calcined at 450° C. for 2 hours to give the calcined catalyst precursor. The calcined catalyst precursor was ground to pass a 850 micron sieve, blended with a 2% wt of graphite and then pelleted. The composition of this catalyst precursor is given in Table 1.

Example 3 (catalyst 3) is a catalyst comprising nickel oxide, alumina and kaolin with magnesium added to reduce silicon loss. To prepare the catalyst precursor 2371g of nickel nitrate hexahydrate and 1175g of aluminium nitrate nonahydrate were dissolved in 4 liters deionised water and heated to 90° C. 168g of Kaolin were to this solution which was stirred until a uniform suspension was obtained. To this suspension was added over a period of 1 hour a solution of 2100g of anhydrous potassium carbonate in 2.5 liters of deionised water. The suspension was vigorously stirred throughout and its temperature maintained at 90° C. When precipitation was complete, the resulting slurry was filtered and the filter cake reslurried with 6 liters of deionised water at 60° C. The process of reslurrying followed by filtration was repeated until the filtrate contained less than 100 ppm of potassium. The moist filter cake (3.15kg with a weight loss on drying at 125° C. followed by calcination at 450° C. of 73.6%) was blended uniformly with an aqueous solution of 358g of magnesium nitrate hexahydrate. The product was then dried at 125° C. and calcined at 450° C. for 2 hours to give the calcined catalyst precursor. The calcined catalyst precursor was ground to pass a 850 micron sieve, blended with 2 wt % of graphite and then pelleted. The composition of this final catalyst precursor is given in Table 1.

Example 4 (catalyst 4) is a catalyst comprising nickel oxide, alumina and kaolin with lanthanum added to reduce silicon loss. To prepare the catalyst precursor 31.8 kg of nickel nitrate hexahydrate and 15.8 kg of aluminium nitrate nonahydrate were dissolved in 80 liters of deionised water and heated to 90° C. 2.05 kg of kaolin were added to this solution and stirred until a uniform suspension was obtained. To this suspension was added over a period of about 1 hour a solution of 24.4 kg of anhydrous sodium carbonate dissolved in 64 liters of deionised water the sodium carbonate solution being at 90° C. The suspension was vigorously stirred throughout and its temperature maintained between 85° and 90° C. When precipitation was completed the resulting slurry was filtered and the filter cake reslurried with 140 liters of deionised water at 60° C. The process of reslurrying followed by filtration was continued until the filtrate contained less than 100 ppm by weight of sodium. A total of three reslurries was required. A 1.24 kg aliquot of the final moist filter cake (75.8% weight loss on drying at 125° C. followed by calcination at 450° C.) was taken and an aqueous solution of 249.3g of lanthanum nitrate hexahydrate was blended uniformly into the moist filter cake. The resultant paste like material was dried at 125° C. and then calcined at 450° C. for 2 hours to give the calcined precursor. The calcined precursor was ground to pass a 850 micron sieve blended with 2 wt % graphite and then pelleted. The composition of the final catalyst precursor is given in Table 1.

Example 5 (catalyst 5) is catalyst comprising nickel oxide, alumina and kaolin with magnesium added to reduce silicon loss. It was prepared as for catalyst 4 (example 4) except that the aqueous solution of lanthanum nitrate hexahydrate was replaced by an aqueous solution of 260.3g magnesium nitrate hexahydrate. The composition of the final catalyst precursor is given in Table 1.

Example 6 (catalyst 6) is a catalyst comprising nickel oxide alumina, kaolin with lanthanum and magnesium added to reduce silicon loss It was prepared as for catalyst 4 (example 4) except that the aqueous solution of lanthanum nitrate hexahydrate was replaced by an aqueous solution of 11.6g of magnesium nitrate hexahydrate and 124.6g lanthanum nitrate hexahydrate. The composition of the final catalyst precursor is given in Table 1.

Example 7 (catalyst 7) is a catalyst comprising nickel oxide, alumina and bentonite with magnesium and potassium added to reduce silicon loss. To prepare the catalyst precursor 5.kg of bentonite clay was placed in a solution containing 2.9 kg of anhydrous sodium carbonate in deionised water. The clay was allowed to swell in this solution overnight. This was then added to a solution containing a further 58 kg of anhydrous sodium carbonate in 100 liters of deionised water and heated to 95° C. 84.4 kg of nickel nitrate hexahydrate and 36.3 kg of aluminium nitrate nonahydrate dissolved in 100 liters of deionised water and heated to 95° C. The precursor was precipitated by slow addition of the carbonates solution to the nitrates solution at a constant temperature of 95° C. Both solutions were vigorously stirred throughout. When precipitation was complete, an aqueous slurry containing 2.9kg of magnesium oxide was added to the mixture and the resulting slurry was maintained at 95° C. for 20 minutes with constant stirring. The slurry was filtered and the filter cake reslurried with 140 liters of deionised water at 60° C. The process of reslurrying followed by filtration was continued until the filtrate contained less than 100 ppm by weight of sodium. The wet mud was then placed in a blender and an aqueous solution of 160 g of anhydrous potassium carbonate was added to it with stirring. The resulting material was dried at 125° C. and then calcined at 450° C. for two hours to give the calcined precursor. The calcined precursor was ground to pass a 850 micron sieve, blended with 2 % by weight of graphite and then pelleted. The composition of the final catalyst precursor is given in Table 1.

Example 8 (catalyst 8) is a catalyst comprising nickel oxide, chromia, alumina and kaolin with magnesium and potassium to reduce silicon loss. A cement binder is also used to improve strength. To prepare the catalyst precursor a solution containing 25.4 kg of anhydous sodium carbonate in 80 liters of deionised water and heated to 75° C. 35.2 kg of nickel nitrate hexahydrate, 13.6 kg of aluminium nitrate nonahydrate and 1.6 kg of chromium nitrate hexahydrate were dissolved in 80 liters of deionised water and heated to 75° C. The precursor was precipitated by slow addition of the carbonates solution to the nitrates solution at a constant temperature of 75° C., both solutions being vigorously stirred throughout. After precipitation an aqueous slurry containing 1.7 kg of kaolin and 0.8 kg of magnesium oxide was added to the solution with stirring. The slurry was filtered and the filter cake reslurried with 140 liters of deionised water at 60° C. The process of reslurrying followed by filtration was continued until the filtrate contained less than 100 ppm by weight of sodium. The resulting material was dried at 125° C. and then calcined at 450° C. for two hours to give the calcined precursor. The calcined precursor was ground to pass a 850 micron sieve, then mixed with 4.95 of Secar 71 high alumina cement, supplied by Lafarge. This powder was further blended with 2 % by weight of graphite and then pelleted. The pelleted catalyst was steamed at atmospheric pressure at 240° C. for 16 hours and then soaked at room temperature in deionised water for over 12 hours. The pellets were dried at 125° C. and then dipped in a solution containing 2 % by weight of potassium hydroxide. The composition of the final catalyst precursor is given in Table 1.

Example 9 (catalyst 9) is a catalyst comprising nickel oxide, chromia, alumina and acid treated montmorillonite with magnesium to reduce silicon loss. To prepare the catalyst precursor 5.1 kg of K10 clay, an acid- activated clay produced by Sud- Chemie, was placed in a solution containing 60.9 kg of anhydrous sodium carbonate in 100 liters of deionised water and heated to 95° C. 84.4 kg of nickel nitrate hexahydrate, 32.6 kg of aluminium nitrate nonahydrate and 3.8 kg of chromium nitrate hexahydrate were dissolved in 100 liters of deionised water and heated to 95° C. The precursor was precipitated by slow addition of the carbonates solution to the nitrates solution at a constant temperature of 95° C, both solutions being vigorously stirred throughout. When precipitation was complete, an aqueous slurry containing 2.9kg of magnesium oxide was added to the mixture and the resulting slurry was maintained at 95° C. for 20 minutes with constant stirring. The slurry was filtered and the filter cake reslurried with 140 liters of deionised water at 60° C. The process of reslurrying followed by filtration was continued until the filtrate contained less than 100 ppm by weight of sodium. The resulting material was dried at 125° C. and then calcined at 450° C. for two hours to give the calcined precursor. The calcined precursor was ground to pass a 850 micron sieve, blended with 2% by weight of graphite and then pelleted. The composition of the final catalyst precursor is given in Table 1.

TABLE 1

| CATALYST PRECURSOR | COMPOSITION | | | | | | | | Nominal Clay Mineral Content wt % |
|---|---|---|---|---|---|---|---|---|---|
| | Ni wt % | Al wt % | Si wt % | Mg wt % | La wt % | C wt % | Cr wt % | K wt % | |
| 1 | 18.5 | 33.4 | 4.4 | — | — | 2.1 | — | — | 20.2 |
| 2 | 41.4 | 12.5 | 5.7 | — | — | 2.0 | — | 0.2 | 27.0 |
| 3 | 46.9 | 11.9 | 3.9 | 3.8 | — | 2.0 | — | — | 17.9 |
| 4 | 41 | 10.1 | 3.0 | — | 16.3 | 2.4 | — | — | 13.8 |
| 5 | 45.4 | 11.0 | 3.2 | 7.2 | — | 2.2 | — | — | 14.7 |
| 6 | 42.0 | 10.3 | 2.9 | 2.9 | 10.8 | 2.1 | — | — | 13.3 |
| 7 | 49.9 | 9.2 | 3.8 | 4.8 | — | 3.9 | — | 0.4 | 17.0 |
| 8 | 36.1 | 18.6 | 1.9 | 2.3 | — | — | 1.0 | 0.5 | 10.0 |
| 9 | 49.6 | 8.1 | 4.2 | 4.9 | — | — | 1.4 | 0.3 | 17.0 |

Compositions analysed by inductively coupled plasma emission spectroscopy. Error in silicon content- +or−0.1 wt %.

The catalyst precursors resulting from Examples 1 to 9 are activated to produce the catalysts by reducing the precursors in hydrogen at 500° C. for 16 hours and at 750 psig at a gas hourly space velocity of 2500 MR$^{-1}$.

The catalysts (except for Catalyst 2) were subjected to a 1000 hour methanation test in a reactor. In the test, gas of a typical composition CO 24.2, $CO_2$ 34.7, $H_2$ 20.2, $CH_4$ 20.5, $C_2H_6$ 0.07 and $N_2$ 0.08 vol % mixed with sufficient steam to give a steam/dry gas ratio of 0.55 was preheated to 320° C. at 750 psig and passed over a bed of each catalyst at 750 psig and a dry gas hourly space velocity of 10,050 hour $^{-1}$. The test for catalyst 2 was identical to that used for the other catalysts except that it was for a duration of only 467 hours (instead of 1000 hours) because the test was terminated on completion of this period as silica had blocked the reactor exit. The reactor was operated in an adiabatic mode and as the gas reacted over the catalyst the temperature rose until 620° C. was attained at which temperature the gas was at equilibrium as regards the methanation and shift reactions. The dry gas composition of the product gas was CO 5.6, $CO_2$ 51.1, $H_2$ 13.6, $CH_4$ 29.6, $C_2H_6$ 0 and $N_2$ 0.9 vol %. The portion of the catalyst bed over which the temperature rises is known as the reaction zone. As the catalyst deactivates the reaction zone extends and the change in zone length can be considered to give a measure of the catalysts ability to maintain its activity under reaction conditions. Values of the rate of change in the zone length for catalysts 1 and 2, the comparative catalysts, relative to catalysts 3 to 9 given in column 2 of Table 2 demonstrate that catalysts 3 to 9 are superior to the comparative catalysts which contained no additive to reduce silicon loss. After completion of a test the catalyst is recovered for examination. The crushing strengths of the recovered pellets and the percentage losses of silicon during the tests are given in columns 4 and 3 of Table 2. The values given in Table 2 demonstrate that the additives in catalysts 3 to 9 do reduce silicon loss whilst at the same time improving their strength retention properties compared to the comparative catalysts.

TABLE 2

| Catalyst | Performance on Methanation Test[1] | % Silicon loss in Methanation Test | Crushing Strength after Methanation Test[2] | |
|---|---|---|---|---|
| | | | A kgf | B % |
| 1 | 1 | 52 | 8.6 | 34.4 |
| 2 | <2.5 | 17 | 15.9 | 61 |
| 3 | 4.1 | 19 | 9.7 | 61 |
| 4 | 6.2 | 7 | 13.3 | 45.3 |
| 5 | 3.1 | 0 | 15.8 | 63.2 |
| 6 | 14.5 | 0 | 18.3 | 73.2 |
| 7 | 7.6 | 5 | 4.9 | 32 |
| 8 | 3.2 | 0 | 32.4 | >78 |
| 9 | 7.1 | 3 | 11.9 | 46 |

[1] $\frac{\text{rate of reaction zone movement for comparative catalyst}}{\text{rate of reaction zone movement for catalyst}}$

[2] Crushing strength: the mean force kg applied along the diameter of the pellets needed to crush them. The results are given both as the measured strength A and as a proportion (%) B of the strength before the methanation test. For Example 8 the strength of the fresh pellets exceeded the maximum measurable by the testing machine.

proportion (%) B of the strength before the methanation test. For Example 8 the strength of the fresh pellets exceeded the maximum measurable by the testing machine.

We claim:

1. A method of preparing a catalyst precursor comprising intimately mixing a Feitknecht compound with a non-calcined alumino-silicate clay mineral to form a mixture and adding at least one stabilising additive for reducing silicon-species loss, said additive comprising an alkaline earth and/or rare earth metal compound, and thereafter calcining the resulting mixture to produce a calcined reaction product forming the catalyst precursor.

2. A method as claimed in claim 1, wherein the Feitknecht compound is coprecipitated in the presence of the clay mineral to provide a mixture of coprecipitated Feitknecht compound and clay mineral and intimately mixing a said additive with said mixture of coprecipitated Feitknecht compound and clay mineral.

3. A method as claimed in claim 1, wherein the Feitknecht compound is coprecipitated in the absence of the clay mineral, and intimately mixing with the coprecipitated Feitknecht compound said additive and the clay mineral.

4. A method as claimed in claim 1, wherein the clay mineral content of the catalyst precursor is from about 2.5 to about 50%.

5. A method as claimed in claim 4, wherein the clay mineral content of the catlyst precursor is from about 10 to about 30%.

6. A method as claimed in claim 1, wherein said Feitknecht compound and said mineral clay are intimately mixed to form a mixture and adding prior to calcination a stabilizing additive comprising an alkaline earth metal compound.

7. A method as claimed in claim 1, wherein the additives are alkaline earth and alkali metal containing compounds and the alkali metal content of the catalyst precursor is not more than about 2.0%.

8. A method as claimed in claim 1, wherein the alkaline earth metal-containing additive is a magnesium compound, the rare earth metal-containing additive is a lanthanum compound, said additive further comprises a potassium compound.

9. A method as claimed in claim 1, wherein the additives are substantially alkaline earth and/or substantially rare earth metal containing compounds, and the total such additive metal content in the catalyst precursor is from about 1 to about 27%.

10. A method as claimed in claim 9, wherein the alkaline-earth-metal containing compound is a magnesium compound and the magnesium content of the catalyst precursor is from about 2.0 to about 8.0%.

11. A method as claimed in claim 10, wherein the clay mineral is a layer-structured phyllosilicate and/or pseudo-layered-structured clay mineral.

12. A method as claimed in claim 11, wherein the pseudo-layer-structured clay mineral is attapulgite.

13. A method as claimed in claim 11, wherein the layer-structured clay mineral is a smectite, or a kaolin.

14. A method as claimed in claim 13, wherein the smectite is bentonite and/or montmorillonite.

15. A method as claimed in claim 14, wherein the kaolin is kaolinite.

16. A method as claimed in claim 15, wherein the additive is a lanthanum compound and the lanthanum content of the catalyst precursor is from about 10 to about 20%.

17. A method as claimed in claim 17, wherein the additive is a calcium compound and the calcium content of the catalyst precursor is from about 6 to about 15%.

18. A method as claimed in claim 15, wherein the additives are magnesium and lanthanum compounds and the combined magnesium and lanthanum content of the catalyst precursor is from about 2 to about 24%.

19. A method as claimed in claim 18, wherein the magnesium content is about 2-4% and the lanthanum content is from about 9 to about 20%.

20. A method as claimed in claim 14 wherein the additives are magnesium and potassium compounds and the magnesium content of the catalyst precursor is about 2-4% whilst the potassium content is from about 0.5 to about 1.0%.

21. A method as claimed in claim 10, wherein the mixture is mixed with a cement binder prior to calcination of the mixture.

22. A method as claimed in claim 1, wherein the calcined catalyst precursor is mixed with a cement binder.

23. A method as claimed in claim 21, wherein the cement binder is an alumina cement binder.

24. A method is claimed in claim 21, wherein the catalyst precursor contains from about 5 to about 15% clay mineral and from about 10 to about 40% cement binder.

25. A method as claimed in claim 24, wherein the catalyst precursor contains from about 20 to about 35% cement binder.

26. A method as claimed in claim 1, wherein the said mixture is autoclaved in a closed vessel prior to calcination.

27. A method as claimed in claim 1, wherein said additive compound is in the form of an aqueous solution, slurry, dispersion or suspension.

28. A method as claimed in claim 1, wherein the clay mineral is mixed in in the form of an aqueous slurry, dispersion or suspension.

29. A catalyst precursor made by a method as claimed in claim 1.

30. A catalyst made by reducing a catalyst precursor as claimed in claim 29.

31. A method as claimed in claim 1 wherein said additive includes an alkali metal compound.

* * * * *